United States Patent
Thomenius et al.

(10) Patent No.: US 7,443,765 B2
(45) Date of Patent: Oct. 28, 2008

(54) RECONFIGURABLE LINEAR SENSOR ARRAYS FOR REDUCED CHANNEL COUNT

(75) Inventors: Kai Erik Thomenius, Clifton Park, NY (US); Rayette Ann Fisher, Niskayuna, NY (US); Robert Gideon Wodnicki, Niskayuna, NY (US); Christopher Robert Hazard, Niskayuna, NY (US); Lowell Scott Smith, Niskayuna, NY (US); Bruno Hans Haider, Ballston Lake, NY (US); Kenneth Wayne Rigby, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 659 days.

(21) Appl. No.: 11/018,238

(22) Filed: Dec. 21, 2004

(65) Prior Publication Data
US 2005/0237858 A1    Oct. 27, 2005

Related U.S. Application Data

(63) Continuation-in-part of application No. 10/383,990, filed on Mar. 6, 2003, now Pat. No. 6,865,140.

(51) Int. Cl.
*G10K 11/00* (2006.01)
*H04R 17/00* (2006.01)

(52) U.S. Cl. .................. 367/154; 367/153; 600/447
(58) Field of Classification Search .................. 367/105, 367/122, 153, 154; 600/447, 459; 342/374, 342/375
See application file for complete search history.

(56) References Cited

U.S. PATENT DOCUMENTS

| | | | |
|---|---|---|---|
| 4,159,462 A * | 6/1979 | Rocha et al. ................. | 367/105 |
| 4,180,790 A * | 12/1979 | Thomas ....................... | 367/105 |
| 4,307,613 A | 12/1981 | Fox | |
| 4,641,660 A | 2/1987 | Bele | |
| 4,658,176 A * | 4/1987 | Nakaya et al. ............... | 310/334 |
| 4,890,267 A | 12/1989 | Rudolph | |
| 5,146,435 A | 9/1992 | Bernstein | |
| 5,452,268 A | 9/1995 | Bernstein | |

(Continued)

FOREIGN PATENT DOCUMENTS

EP    0040375    11/1981

(Continued)

OTHER PUBLICATIONS

Ladabaum et al., Surface Micromachined Capacitive Ultrasonic Transducers, IEEE Trans. Ultrasonics, Ferroelectrics and Frequency Control, vol. 45, No. 3, May 1998, pp. 678-690.

(Continued)

*Primary Examiner*—Ian J Lobo
(74) *Attorney, Agent, or Firm*—Fletcher Yoder

(57) ABSTRACT

A reconfigurable linear array of sensors (e.g., optical, thermal, pressure, ultrasonic). The reconfigurability allows the size and spacing of the sensor elements to be a function of the distance from the beam center. This feature improves performance for imaging systems having a limited channel count. The improved performance, for applications in which multiple transmit focal zones are employed, arises from the ability to adjust the aperture for a particular depth.

35 Claims, 10 Drawing Sheets

U.S. PATENT DOCUMENTS

| | | |
|---|---|---|
| 5,558,623 A | 9/1996 | Cody |
| 5,569,968 A | 10/1996 | Lal et al. |
| 5,596,222 A | 1/1997 | Bernstein |
| 5,619,476 A | 4/1997 | Haller et al. |
| 5,684,324 A | 11/1997 | Bernstein |
| 5,732,706 A | 3/1998 | White et al. |
| 5,870,351 A | 2/1999 | Ladabaum et al. |
| 5,894,452 A | 4/1999 | Ladabaum et al. |
| 5,902,241 A | 5/1999 | Seyed-Bolorforosh et al. |
| 5,982,709 A | 11/1999 | Ladabaum et al. |
| 6,004,832 A | 12/1999 | Haller et al. |
| 6,120,449 A | 9/2000 | Snyder |
| 6,292,435 B1 | 9/2001 | Savord et al. |
| 6,320,239 B1 | 11/2001 | Eccardt et al. |
| 6,325,757 B1 | 12/2001 | Erikson et al. |
| 6,328,697 B1 | 12/2001 | Fraser |
| 6,359,367 B1 | 3/2002 | Sumanaweera et al. |
| 6,381,197 B1 | 4/2002 | Savord et al. |
| 6,384,516 B1 | 5/2002 | Fraser |
| 6,443,901 B1 | 9/2002 | Fraser |
| 6,503,204 B1 | 1/2003 | Sumanaweera et al. |
| 6,571,445 B2 | 6/2003 | Ladabaum |
| 6,585,653 B2 | 7/2003 | Miller |
| 6,589,180 B2 | 7/2003 | Erikson et al. |
| 6,736,779 B1 | 5/2004 | Sano et al. |
| 2002/0048219 A1 | 4/2002 | Ladabaum et al. |
| 2005/0057284 A1* | 3/2005 | Wodnicki ............ 327/100 |

FOREIGN PATENT DOCUMENTS

| | | |
|---|---|---|
| EP | 1026663 | 8/2000 |
| WO | WO 00/05001 | 3/2000 |

OTHER PUBLICATIONS

Dietz et al., Wideband Annular Array Response, 1978 Ultrasonics Symp. Proc., pp. 206-211.

Bailey et al., A Computer-Controlled Transducer for Real-Time Three- Dimensional Imaging, Acoustical Imaging, vol. 18, Editors: Lee and Wade, Plenum Press, New York, 1991, pp. 543-551.

Ergun et al., Fabrication and Characterization of 1-Dimensional and 2- Dimensional CMUT Arrays etc., IEEE, 2002, pp. 2361-2367.

Oralkum et al., Capacitive Micromachined Ultrasonic Transducers: Next-Generation Arrays for Acoustic Imaging, IEEE Trans. Ultrasonics, Ferroelectronics, and Freq. control, vol. 29, No. 11, Nov. 2002, pp. 1596-1610.

Jin et al., Micromachined Capacitive Ultrasonic Immersion Transducer for Medical Imaging, Proc. 20th Annual Int'l Conf. IEEE Engineering in Medicine and Biology Society, vol. 20, No. 2, 1998, pp. 779-782.

* cited by examiner

DELAY PROFILE

SORTED DELAYS WITH EQUAL DELAY RANGES

QUANTIZED DELAY PROFILE

RECONFIGURABLE LINEAR SENSOR ARRAYS FOR REDUCED CHANNEL COUNT

RELATED PATENT APPLICATION

This application is a continuation-in-part of and claims priority from U.S. patent application Ser. No. 10/383,990 filed on Mar. 6, 2003 now U.S. Pat. No. 6,865,140 and entitled "Mosaic Arrays Using Micromachined Ultrasound Transducers".

STATEMENT REGARDING FEDERALLY SPONSORED RESEARCH AND DEVELOPMENT

The United States Government may have certain rights in this invention pursuant to U.S. Government Contract Number DAMD17-02-1-0181 awarded by the U.S. Army.

BACKGROUND OF THE INVENTION

This invention generally relates to reconfigurable arrays of sensors (e.g., optical, thermal, pressure, ultrasonic). In particular, the invention relates to reconfigurable micromachined ultrasonic transducer (MUT) arrays. One specific application for MUTs is in medical diagnostic ultrasound imaging systems. Another specific example is for non-destructive evaluation (NDE) of materials, such as castings, forgings, or pipelines.

Conventional ultrasound imaging systems comprise an array of ultrasonic transducers that are used to transmit an ultrasound beam and then receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is continuously refocused along the scan line as the reflected ultrasonic waves are received.

For ultrasound imaging, the array typically has a multiplicity of transducers arranged in one or more rows and driven with separate voltages in transmit. By selecting the time delay (or phase) and amplitude of the applied voltages, the individual transducers in a given row can be controlled to produce ultrasonic waves that combine to form a net ultrasonic wave that travels along a preferred vector direction and is focused in a selected zone along the beam.

The same principles apply when the transducer probe is employed to receive the reflected sound in a receive mode. The voltages produced at the receiving transducers are summed so that the net signal is indicative of the ultrasound reflected from a single focal zone in the object. As with the transmission mode, this focused reception of the ultrasonic energy is achieved by imparting separate time delay (and/or phase shifts) and gains to the signal from each receiving transducer. The time delays are adjusted with increasing depth of the returned signal to provide dynamic focusing on receive.

The quality or resolution of the image formed is partly a function of the number of transducers that respectively constitute the transmit and receive apertures of the transducer array. Accordingly, to achieve high image quality, a large number of transducers is desirable for both two- and three-dimensional imaging applications. The ultrasound transducers are typically located in a hand-held transducer probe that is connected by a flexible cable to an electronics unit that processes the transducer signals and generates ultrasound images. The transducer probe may carry both ultrasound transmit circuitry and ultrasound receive circuitry.

A reconfigurable ultrasound array is one that allows groups of subelements to be connected together dynamically so that the shape of the resulting element can be made to match the shape of the wave front. This can lead to improved performance and/or reduced channel count. Reconfigurability can be achieved using a switching network.

One advantage of MUTs is that they can be made using semiconductor fabrication processes, such as microfabrication processes grouped under the heading "micromachining". As explained in U.S. Pat. No. 6,359,367:

> Micromachining is the formation of microscopic structures using a combination or subset of (A) Patterning tools (generally lithography such as projection-aligners or wafer-steppers), and (B) Deposition tools such as PVD (physical vapor deposition), CVD (chemical vapor deposition), LPCVD (low-pressure chemical vapor deposition), PECVD (plasma chemical vapor deposition), and (C) Etching tools such as wet-chemical etching, plasma-etching, ion-milling, sputter-etching or laser-etching. Micromachining is typically performed on substrates or wafers made of silicon, glass, sapphire or ceramic. Such substrates or wafers are generally very flat and smooth and have lateral dimensions in inches. They are usually processed as groups in cassettes as they travel from process tool to process tool. Each substrate can advantageously (but not necessarily) incorporate numerous copies of the product. There are two generic types of micromachining . . . 1) Bulk micromachining wherein the wafer or substrate has large portions of its thickness sculptured, and 2) Surface micromachining wherein the sculpturing is generally limited to the surface, and particularly to thin deposited films on the surface. The micromachining definition used herein includes the use of conventional or known micromachinable materials including silicon, sapphire, glass materials of all types, polymers (such as polyimide), polysilicon, silicon nitride, silicon oxynitride, thin film metals such as aluminum alloys, copper alloys and tungsten, spin-on-glasses (SOGs), implantable or diffused dopants and grown films such as silicon oxides and nitrides.

The same definition of micromachining is adopted herein. The systems resulting from such micromachining processes are typically referred to as "micromachined electro-mechanical systems (MEMS).

The cMUTs are usually hexagonal-shaped structures that have a membrane stretched across them. This membrane is held close to the substrate surface by an applied bias voltage. By applying an oscillatory signal to the already biased cMUT, the membrane can be made to vibrate, thus allowing it to radiate acoustical energy. Likewise, when acoustic waves are incident on the membrane the resulting vibrations can be detected as voltage changes on the cMUT. A cMUT cell is the term used to describe a single one of these hexagonal "drum" structures. The cMUT cells can be very small structures. Typical cell dimensions are 25-50 microns from flat edge to flat edge on the hexagon. The dimensions of the cells are in many ways dictated by the designed acoustical response. It may not be possible to create larger cells that still perform well in terms of frequency response and sensitivity desired.

It is difficult to produce electronics that would allow individual control over such small cells. While in terms of the acoustical performance of the array as whole, the small cell size is excellent and leads to great flexibility, control is limited to larger structures. Grouping together multiple cells and connecting them electrically allows one to create a larger subelement, which can have the individual control while maintaining the desired acoustical response. So a subelement is a group of electrically connected cells that cannot be reconfigured. For the purpose of this disclosure, the subelement is the smallest independently controlled acoustical unit. One can form elements by connecting subelements together using a switching network. The elements can be reconfigured by changing the state of the switching network. However, subelements comprise connected cells that are not switchably disconnectable and thus cannot be reconfigured.

The current trend in ultrasound systems is toward smaller more portable devices. Perhaps one day a small palm-sized ultrasound system will replace the stethoscope as the physician's standard equipment. In order to realize such small ultrasound systems, reducing the number of beamforming channels is a must. The basic problem is to maintain adequate beamforming performance (resolution and contrast) while reducing the number of system channels. In order to maintain resolution, the aperture must not be reduced. This means for a standard array that either the number of channels must increase with increasing aperture size, or the spacing between them must increase. Increasing the step size in a uniform manner across the array results in grating lobes, which are not desirable.

All current ultrasound linear array probes have a constant pitch. Reducing channel count usually means giving up aperture or tolerating grating lobes. One method that reduces channel count without grating lobes is beamformer folding. For linear arrays the delays on either side of the beam center are symmetrical. This means that a reduction in channels by about one half can be achieved by allowing a multiplexing scheme that connects these symmetric elements to the same system channel. However, this multiplexing scheme can become very complicated for large numbers of system channels. Also, current multiplexing schemes cannot provide complete reconfigurability because they are limited to relatively large size elements at fixed locations. Another way that can be used to increase channel count is the use of synthetic aperture schemes. Here a larger aperture is built up over multiple transmits. This can lead to significant channel count reduction, but suffers from reduced signal-to-noise ratios and loss of frame rate due to the requirement of multiple firings. Motion can also introduce artifacts in the synthetic aperture images.

There is a need for a reduced channel count system that maintains aperture size and does not have grating lobes.

BRIEF DESCRIPTION OF THE INVENTION

The present invention is directed to a reconfigurable linear arrays of micromachined sensors (e.g., optical, thermal, pressure, ultrasonic). The reconfigurability allows the size and spacing of the sensor elements to be a function of the distance from the beam center. This feature improves performance for imaging systems having a limited channel count. The improved performance, for applications in which multiple transmit focal zones are employed, arises from the ability to adjust the aperture for a particular depth.

One aspect of the invention is an apparatus comprising: a multiplicity of sensor subelements disposed in side-by-side relationship along a line to form a row, each of the sensor subelements comprising a respective multiplicity of electromechanical devices occupying an approximately rectangular area; a multiplicity of electrically conductive access lines; a multiplicity of access switches, each of the access switches electrically connecting a respective one of the sensor subelements to one of the access lines when the access switch is turned on; a multiplicity of matrix switches, each of the matrix switches electrically connecting a respective one of the sensor subelements to a respective adjacent one of the sensor subelements when the matrix switch is turned on; a multiplicity of switch state control circuits, each of the switch state control circuits controlling the states of a respective one of the access switches and a respective one of the matrix switches; and a programming circuit electrically connected for programming the switch state control circuits in accordance with selected switch configurations corresponding to respective apertures.

Another aspect of the invention is a device comprising: a multiplicity of approximately rectangular sensor subelements disposed in side-by-side relationship along a line to form a row in a first stratum; a multiplicity of interface electronics cells disposed in side-by-side relationship along a line to form a row in a second stratum fixed relative to and underlying the first stratum, with each interface electronics cell underlying a respective sensor subelement; a multiplicity of electrical connections, each of the electrical connections electrically connecting a respective one of the interface electronics cells to a respective one of the sensor subelements; and a multiplicity of electrically conductive access lines, wherein each of the unit electronics cells comprises: an access switch that electrically connects the respective sensor subelement to one of the access lines when the access switch is turned on; a matrix switch that electrically connects the respective sensor subelements to a respective adjacent one of the sensor subelements when the matrix switch is turned on; and switch state control circuitry that controls the states of the access and matrix switches.

A further aspect of the invention is a system comprising: a linear array of ultrasonic transducer subelements each having an active area that is approximately rectangular; a multiplicity of matrix switches disposed to selectively electrically couple ultrasonic transducer subelements to each other to form ultrasonic transducer elements when the matrix switches are selectively turned on; a multiplicity of electrically conductive access lines running substantially parallel to the linear array; a multiplicity of access switches disposed to selectively electrically couple ultrasonic transducer elements to access lines when the access switches are selectively turned on; a multiplicity of system channels; and a multiplexer having a state whereby each of the access lines is electrically coupled to a respective one of the system channels via the multiplexer, wherein each of the ultrasonic transducer subelements comprises a respective multiplicity of electrically connected and not switchably disconnectable MUT cells.

Yet another aspect of the invention is a system comprising: a linear array of ultrasonic transducer subelements each having an active area that is approximately rectangular; a multiplicity of access lines; and a switching network comprising a first set of switches for electrically connecting selected ultrasonic transducer subelements to each other to form ultrasonic transducer elements, and a second set of switches for electrically coupling the ultrasonic transducer elements to selected access lines, the first and second sets of switches being set in accordance with a switching configuration to form an aperture, wherein the pitch and width of the ultrasonic transducer elements making up the aperture vary across the linear array.

Other aspects of the invention are disclosed and claimed below.

BRIEF DESCRIPTION OF THE DRAWINGS

Reference will now be made to the drawings in which similar elements in different drawings bear the same reference numerals.

DETAILED DESCRIPTION OF THE INVENTION

The invention is directed to a reconfigurable switching matrix that can be utilized to vary the size and spacing of an associated linear array of sensors to be functions of the distance from the beam center. For the purposes of illustration, the reconfigurable linear array will be described with reference to capacitive micromachined ultrasonic transducers (cMUTs). However, it should be understood that the aspects of the invention disclosed herein are not limited in their application to probes employing cMUTs.

Figure 1:
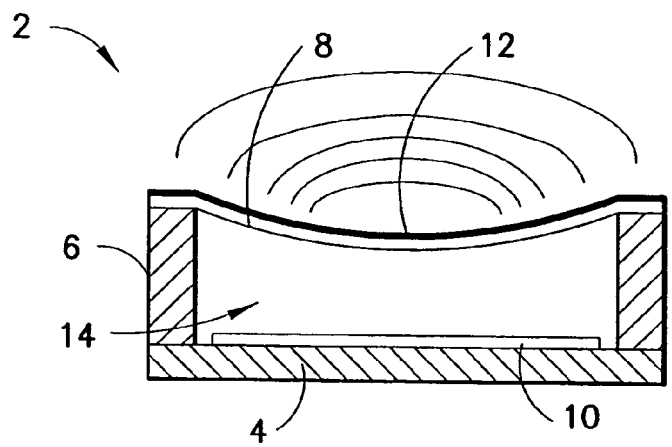
FIG. 1 is a drawing showing a cross-sectional view of a typical cMUT cell.

Referring to FIG. 1, a typical cMUT transducer cell 2 is shown in cross section. An array of such cMUT transducer cells is typically fabricated on a substrate 4, such as a heavily doped silicon (hence, semiconductive) wafer. For each cMUT transducer cell, a thin membrane or diaphragm 8, which may be made of silicon nitride, is suspended above the substrate 4. The membrane 8 is supported on its periphery by an insulating support 6, which may be made of silicon oxide or silicon nitride. The cavity 14 between the membrane 8 and the substrate 4 may be air- or gas-filled or wholly or partially evacuated. Typically, cMUTs are evacuated as completely as the processes allow. A film or layer of conductive material, such as aluminum alloy or other suitable conductive material, forms an electrode 12 on the membrane 8, and another film or layer made of conductive material forms an electrode 10 on the substrate 4. Alternatively, the bottom electrode can be formed by appropriate doping of the semiconductive substrate 4.

The two electrodes 10 and 12, separated by the cavity 14, form a capacitance. When an impinging acoustic signal causes the membrane 8 to vibrate, the variation in the capacitance can be detected using associated electronics (not shown in FIG. 1), thereby transducing the acoustic signal into an electrical signal. Conversely, an AC signal applied to one of the electrodes will modulate the charge on the electrode, which in turn causes a modulation in the capacitive force between the electrodes, the latter causing the diaphragm to move and thereby transmit an acoustic signal.

The individual cells can have round, rectangular, hexagonal, or other peripheral shapes. Hexagonal shapes provide dense packing of the cMUT cells of a transducer subelement. The cMUT cells can have different dimensions so that the transducer subelement will have composite characteristics of the different cell sizes, giving the transducer a broadband characteristic.

Unfortunately, it is difficult to produce electronics that would allow individual control over such small cells. While in terms of the acoustical performance of the array as a whole, the small cell size is excellent and leads to great flexibility, control is limited to larger structures. Grouping together multiple cells and connecting them electrically allows one to create a larger subelement, which can have the individual control while maintaining the desired acoustical response. One can form rings or elements by connecting subelements together using a switching network. The elements can be reconfigured by changing the state of the switching network. However, individual subelements cannot be reconfigured to form different subelements.

MUT cells can be connected together in the micromachining process to form subelements, using the manufacturing techniques disclosed in U.S. Pat. No. 6,571,445. The MUT cells are thus connected without intervening switches (i.e., the MUT cells are not switchably disconnectable from each other). The term "acoustical subelement" will be used in the following to describe such a cluster. These acoustical subelements will in turn be interconnected by microelectronic switches to form larger elements by placing such switches within the silicon layer or on a different substrate situated directly adjacent to the transducer array.

As used herein, the term "acoustical subelement" is a single cell or a group of electrically connected cells that cannot be reconfigured, i.e., the subelement is the smallest independently controlled acoustical unit. The term "subelement" means an acoustical subelement and its associated integrated electronics. An "element" is formed by connecting subelements together using a switching network. The elements can be reconfigured by changing the state of the switching network. At least some of the switches included in the switching network are part of the "associated integrated electronics", as explained in greater detail below.

Figure 2:
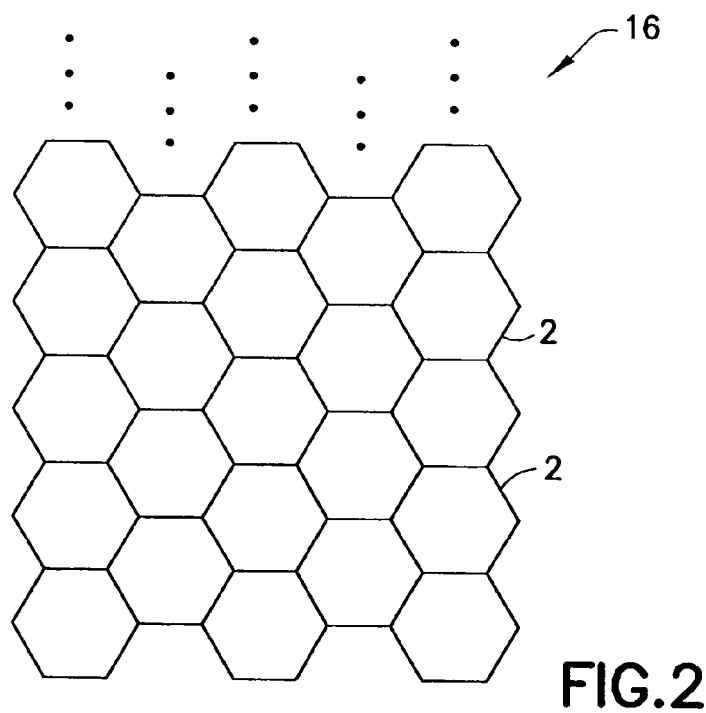
FIG. 2 is a drawing showing hexagonal MUT cells of a subelement of a linear transducer array in accordance with one embodiment of the invention.
Figure 3:
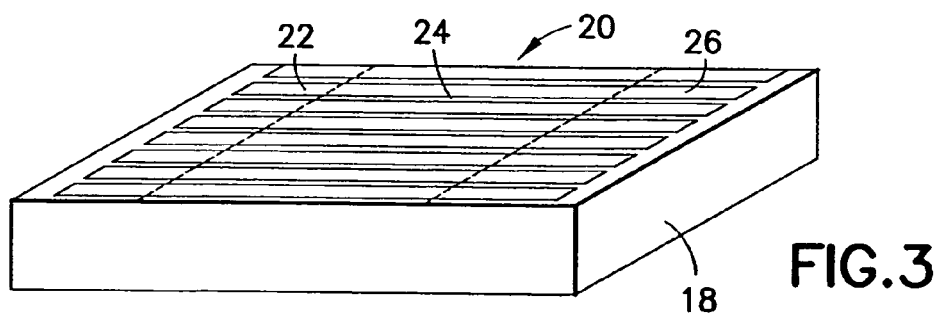
FIG. 3 is a drawing showing an isometric view of a micromachined structure comprising a one-dimensional or 1.5 dimensional array of transducer elements made from cMUT cells.

As disclosed in U.S. patent application Ser. No. 10/383,990, a transducer subelement can be formed by interconnecting a group of hexagonal cMUT cells. The top electrodes of each cMUT cell in the subelement are electrically coupled together by connections that are not switchably disconnectable. In the case of a hexagonal array, six conductors radiate outward from the top electrode (not shown in the drawings) and are respectively connected to the top electrodes of the neighboring cMUT cells (except in the case of cells on the periphery, which connect to three, not six, other cells). Similarly, the bottom electrodes of each cell in the subelement are electrically coupled together by connections that are not switchably disconnectable. A portion of one subelement 16 having five columns of cells 2, the columns extending as far as necessary to fill the given subelement size, is shown in FIG. 2. Alternatively, linear arrays may be constructed having subelements comprising more or less than five columns of cMUT cells A design for a linear array of elements made up of cMUT cells is generally depicted in FIG. 3. In this example, a multiplicity of cMUT cells are built on a CMOS wafer 18 using micromachining techniques. The cMUT cells are arranged to form a single row of ultrasonic transducer elements 20 arrayed in an azimuthal direction, each element 20 covering an approximately rectangular area with the elements arrayed in a side-by-side relationship. The cMUT cells of each element 20 are connected in parallel. Each element 20 may comprise 100 to 1,000 cMUT cells (i.e., any number that is necessary to fill the given subelement size). For example, a subelement may comprise a multiplicity of hexagonal cells arranged in six columns, each column having on the order of 100 cells and being generally aligned with an elevational direction. The cMUT cells of a subelement all resonate together to generate an ultrasound wavefront. These subelements can, in turn, be switchably connected to form transducer elements of varying size and spacing.

To provide a 1.5-dimensional transducer array, each generally rectangular region may be divided into three approximately rectangular subregions 22, 24, and 26, as indicated by dashed lines in FIG. 3. The lengths of subregions 22 and 26 are equal and typically (but not necessarily) less than the length of the central subregion 24. In accordance with this alternative embodiment, the cMUT cells in subregion 22 are interconnected together and are not switchably disconnectable from each other; the cMUT cells in subregion 24 are interconnected together and are not switchably disconnectable from each other; and the cMUT cells in subregion 26 are interconnected together and are not switchably disconnectable from each other, thus forming three subelements in each column. In this case, the cMUT cells of subregions 22 and 26 are preferably activated concurrently during transmission, but in some configurations they can be independent.

Naturally, the foregoing concept can be extrapolated to build probes having more than three rows of transducer elements.

The invention disclosed herein seeks to exploit reconfigurability as a means of reducing channel count. Reconfigurability can mean different things. A fully reconfigurable array has the ability to connect any subelement from a two-dimensional array to any system channel. The underlying two-dimensional array can have overall dimensions that are equivalent to current transducer arrays, or it can have elevation dimensions that are larger than current arrays. To be reconfigurable also means that this mapping from subelements to system channels can be changed dynamically. For example, one may wish to reconfigure the array for each beam in an image or for each focal depth. Or one may wish to have different configurations on transmit versus receive. If one wanted to push the technology even further, one would like to be able to continuously vary the configuration as a function of depth during receive. In practice, providing reconfigurability can be a challenge; especially the dynamic receive reconfigurability described. As a result, one may prefer to deal with more restricted cases of reconfigurability.

Figure 4:
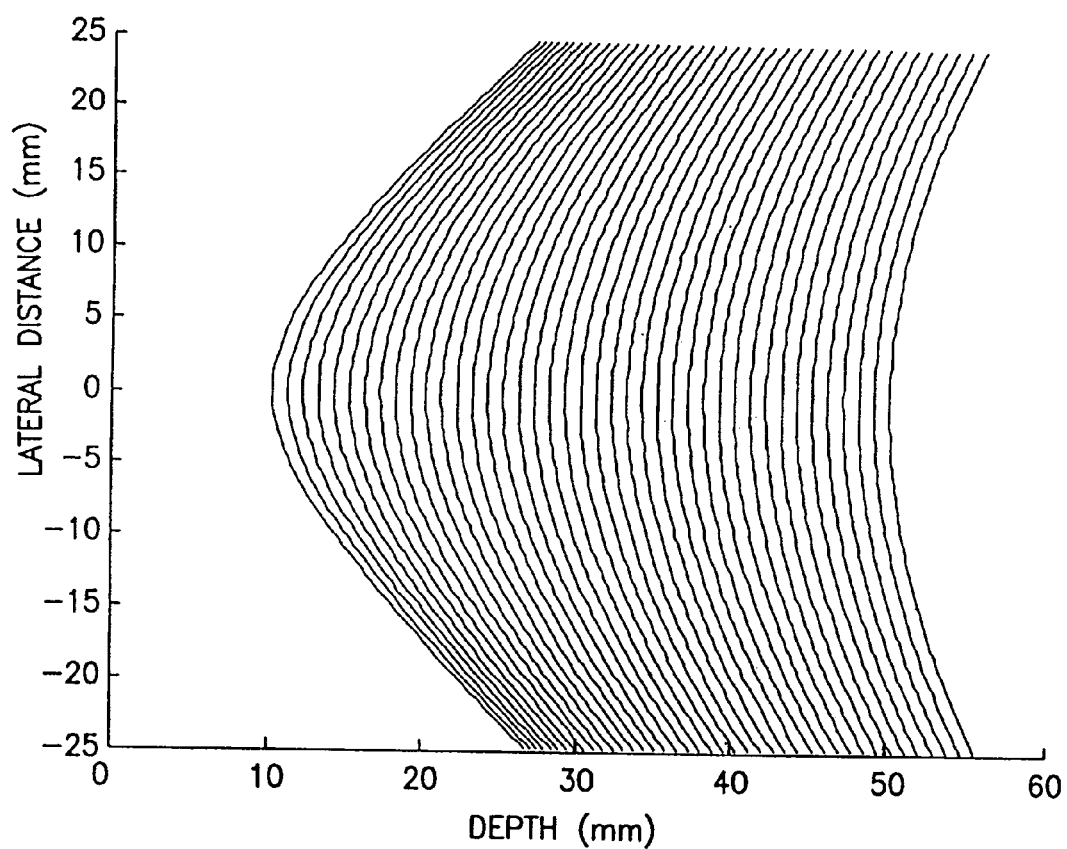
FIG. 4 is a graph showing how the delay profiles across an aperture (i.e., lateral distance) change with increasing depth in a linear transducer array.

FIG. 4 shows how the delay profiles across an aperture change with increasing depth in a linear transducer array. In the near field (i.e., at shallow depths) the delays change rapidly as one moves from the center of the aperture outward, toward the edges. As the depth increases, the delay profiles flatten and the change from the center of the aperture to the edge is more gradual (i.e., the changes are smaller).

Figure 5:
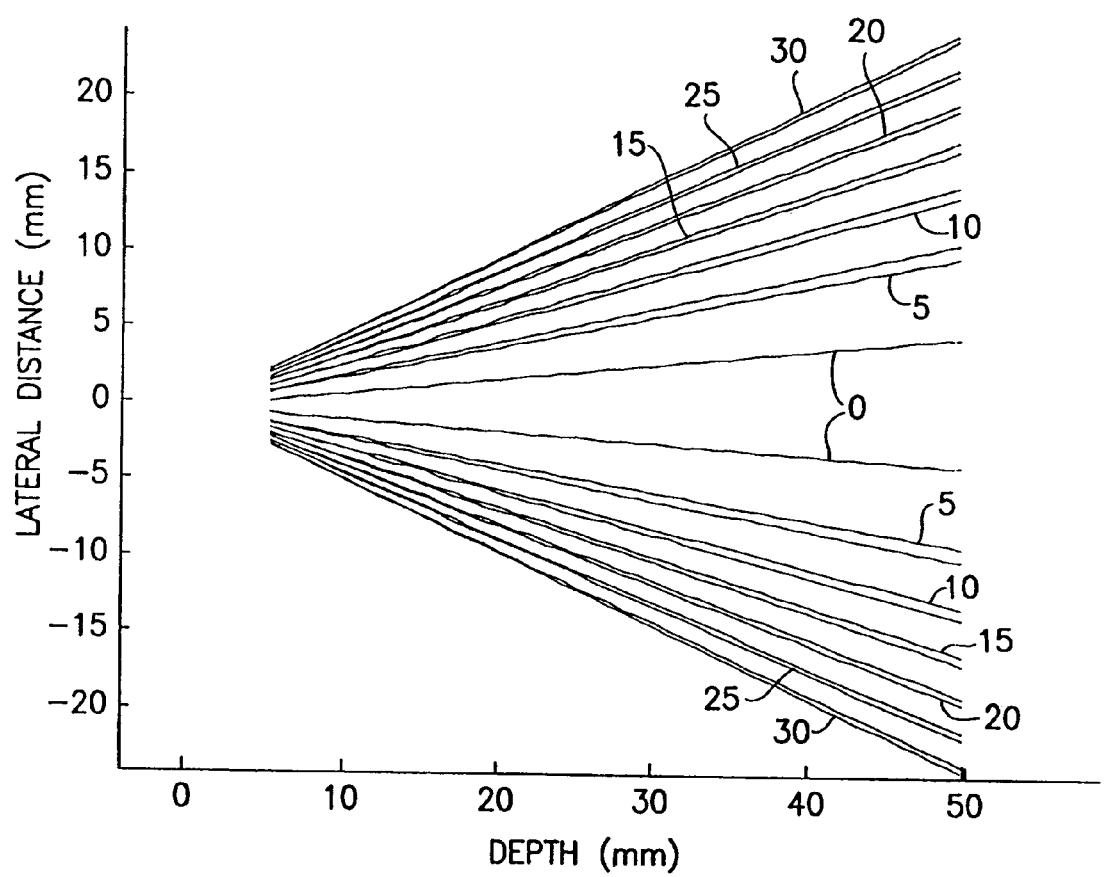
FIG. 5 is a graph showing how a completely dynamic reconfigurable aperture would grow as a function of increasing depth in a linear transducer array.

FIG. 5 shows how a completely dynamic reconfigurable aperture would grow as a function of increasing depth. Here the reconfigurability has been restricted to the azimuthal dimension. The two lines at the center represent the borders of the central element. Every fifth element is shown. This type of reconfigurability provides the most advantage because in the near field it allows all of the channels to be used despite the smaller aperture, as opposed to simply turning off channels for which the delay errors are large. The elements expand as the depth increases. Reconfigurability takes advantage of the fact that the delay profile flattens as depth increases. This means that the individual elements can grow in size with increasing depth without an increase in the delay error across those elements. Without reconfigurability, the size of the elements would be determined by the required sampling at the outer edge of the aperture, for the shallowest imaging depth. This means to get the same delay error across the elements, one would need many more channels. But if the array can dynamically change the size and pitch of the elements, it can be configured to take advantage of the depth-dependent delay curves.

An ideal implementation of linear array reconfigurability would allow the configuration to change dynamically as a function of depth. This reconfigurability would occur in many discrete steps. This type of reconfigurability requires very fast switching between configurations with virtually no noise. Specialized mixed analog and digital circuitry would be required.

To provide for quick, low-power, low-noise reconfiguration of switch states, local buffering of all depth configurations for a line could be used. For example, in an integrated reconfigurable linear switching array where up to ten different depth zones are required for each line, ten local buffers would be integrated on the same chip for each switch in the array. Before a given line is imaged, all ten buffers for the switch would be loaded. Then during line imaging, at each depth transition, data from the respective buffer would be selected for the given switch.

Digital noise is coupled to sensitive analog circuitry by coupling through shared substrates and input pads. By storing data locally, noise coupling due to this effect is reduced. In addition, this technique leads to increased transition speed since locally buffered data is only transmitted the short on-chip distance rather than the distance from the probe control electronics or even from the system electronics. With co-integrated DRAM, it should be possible to store switch configuration states for an entire scan locally on the same chip as the switches, which would reduce power since one need program the switches only once for a particular operating mode. Further savings could be realized by reprogramming only those switches that change for each configuration change with depth.

Figure 6:
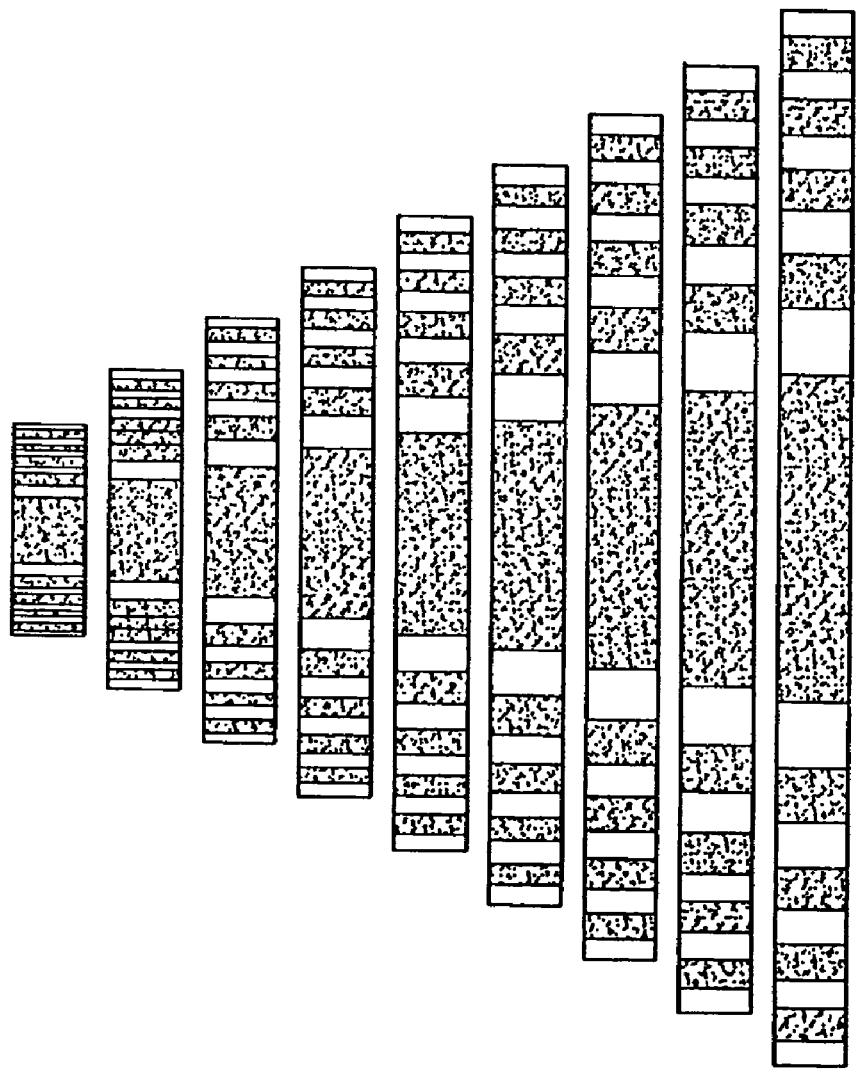
FIG. 6 is a drawing showing an aperture of a linear transducer array as it grows and reconfigures with increasing depth. The shaded areas represent array elements that are connected to respective system channels.
Figure 6:
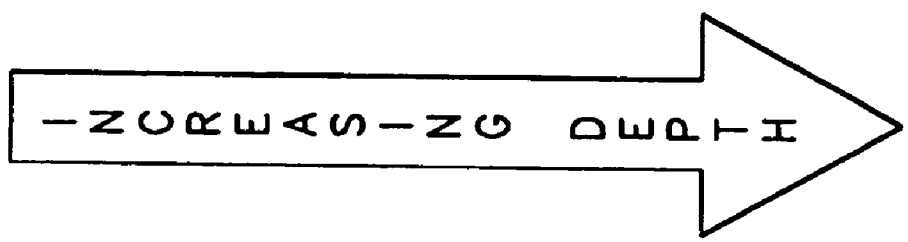

In a linear reconfigurable array that is to be used in a low-power system, a minimum number of switch changes is desired when moving from one aperture to the next. The number of switch changes can be minimized by maintaining a local memory within each respective control circuit at each element. The initial pattern is written into the elements at the beginning of an imaging sequence. FIG. 6 shows an aperture as it grows and reconfigures with increasing depth. The shaded areas represent array elements that are connected to system channels via respective access switches. As the pattern shown in FIG. 6 grows, channel mappings shift out from the center and grow slightly at each transmit state. This change in the pattern can be efficiently accomplished by shifting the existing pattern out (left for left half of array, right for right half) while at the same time reprogramming only those access and matrix switches that need to be reprogrammed to adjust the pattern as it grows. For improved noise performance, switch states can be buffered, and next state adjustments spread out over the entire available programming time.

An alternative implementation would not allow reconfigurability during reception, but would instead break the depth of field up into multiple focal zones. A different transmit and receive cycle would be required for each zone, so this implementation would be limited to those cases where frame rate is not a concern or where imaging depths are not great. For each of the zones there would be a new configuration that would try to optimize the element size and distribution for that particular focal zone. This multiple zone approach gives the advantage of using all the channels in the near field without having to implement the reconfigurability in a way that allows reconfiguration along the depth of a single reception. FIG. 6 shows how the elements might be reorganized with depth, either for particular zones or in a more dynamic fashion.

Figure 7:
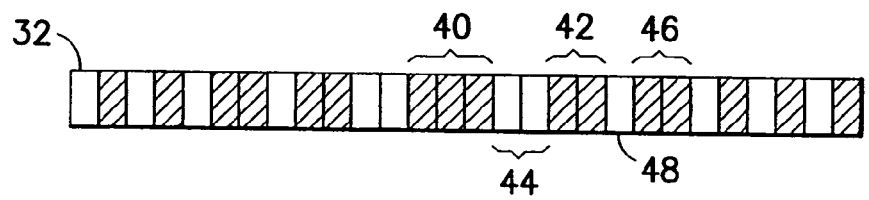
FIG. 7 is a drawing showing an aperture of a linear transducer array having elements of varying width and pitch. The hatched areas represent array elements that are connected to respective system channels.

As shown in FIG. 7, the width of an element is determined by the number of adjacent acoustical subelements that have been interconnected to each other by matrix switches (not shown in FIG. 7). The location of an element is determined by which adjacent acoustical subelements are interconnected to each other. The aperture depicted in FIG. 7 comprises an element 40 formed by interconnecting three adjacent acoustical subelements; an element 42 formed by interconnecting two adjacent acoustical subelements, element 42 being separated from element 40 by two disconnected acoustical subelements; an element 46 formed by interconnecting two adjacent acoustical subelements 44, element 46 being separated from element 42 by one disconnected acoustical subelement 48; and so forth.

For one-dimensional arrays, one can have size and shape reconfigurability if one has very thin columns of MUT cells that can be selectively connected to any or a number of system channels. Each column comprises a respective multiplicity of interconnected MUT cells (not switchably disconnectable from each other) that form a respective acoustical subelement. Each element, which is defined as the one or more acoustical subelements that are connected to a particular system channel, is formed by connecting the appropriate acoustical subelements (i.e., columns of MUT cells) to each other and connecting the system channel to that group of connected acoustical subelements.

Figure 8:
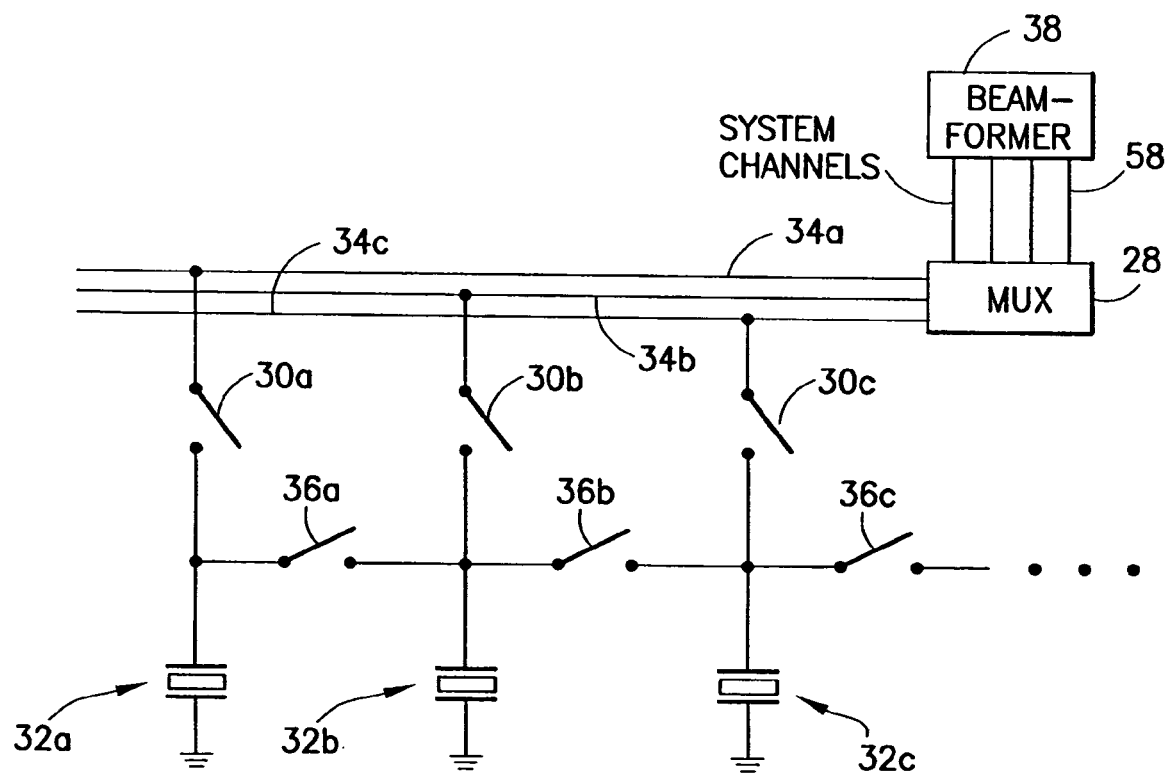
FIG. 8 is a diagram showing various switches for connecting acoustical subelements to each other and to system channels in accordance with one embodiment of the invention.

A portion of a row of transducer elements of a linear array in accordance with one embodiment of the invention is shown in FIG. 8. Each element in the array comprises a respective acoustical subelement and a respective switching network. The switching network in turn comprises an access switch for connecting the associated acoustical subelement to an access line and a matrix switch for connecting the associated acoustical subelement to an adjacent acoustical subelement. FIG. 8 shows three acoustical subelements 32a, 32b and 32c (each comprising a respective column of interconnected MUT cells) that are respectively switchably connectable to selected system channels 58 by way of respective access switches 30a, 30b and 30c; respective access lines 34a, 34b and 34c; and a multiplexer 28. FIG. 8 further shows three matrix switches 36a, 36b and 36c for electrically coupling selected acoustical subelements to each other. This allows any number of acoustical subelements to be coupled to form a single element. For example, matrix switch 36a can be closed to connect acoustical subelements 32a and 32b to each other; likewise, matrix switch 36b can be closed to connect acoustical subelements 32b and 32c to each other. Matrix switches 36a and 36b can be closed at the same time to connect acoustical subelements 32a, 32b and 32c to each other. Similarly, matrix switch 36c can be closed to connect the next acoustical subelement (not shown in FIG. 8) to acoustical subelement 32c. The resulting elements are then connected to the multiplexer 28 by way of respective access switches. Precisely which access switches are employed is dependent on the particular switch configuration. For example, if acoustical subelements 32a and 32b are connected to each other via closed matrix switch 36a, then the resulting element can be connected to the multiplexer 28 via either access switch 30a or access switch 30b. Extrapolating this concept, if acoustical subelements 32a, 32b and 32c are connected to each other via closed matrix switches 36a and 36b, then the resulting element can be connected to the multiplexer 28 via any one of access switches 30a, 30b and 30c. The state of the multiplexer 28 determines which of system channels 58 the respective element is connected to. The multiplexer can be disposed in a marginal area outside the footprint of the row (or rows) of acoustical subelements (see, e.g., FIG. 7). The system channels 58 carry acquired acoustic data to the beamformer 38 of an ultrasound imaging system. Other well-known components of a typical ultrasound image system, such as an operator interface, a host computer, an image processor, a scan controller, a video processor, a display monitor, etc. are not shown in FIG. 8.

As shown in FIG. 8, multiple access lines can be used per row of acoustical subelements. The access switches are staggered as shown in FIG. 8 to reduce the number required for a given number of access lines. Random ordering of access switches to bus lines (not shown) could also be employed to reduce artifacts due to the repeating patterns. More than one access switch in each subelement could be used to improve the flexibility of the array. In such an architecture, a tradeoff between flexibility and number of access switches per subelement would be made where the number is still significantly fewer than the number of access lines and system channels. It is also possible to use more than one access switch per access line in each element. This would improve the yield of the device since non-functioning access switches could be bypassed using the redundant access switches.

In accordance with an alternative embodiment of the invention, a full cross-point switching matrix can be utilized. This would enable each acoustical subelement to be connected to any system channel. This can be achieved by providing a switch for each channel associated with each subelement. In this case, a respective access line is provided for every channel and a respective access switch is provided for every access line for each subelement. This full cross-point switching matrix has some redundancy. Because all channels are equivalent, a half cross-point switching matrix could be used. In both these cases, there is a direct connection from the acoustical subelement to the access line and no matrix switches are required.

The thickness of the columns of MUT cells making up a row of acoustical subelements should be kept small to allow a flexible reconfiguration. However, the switching electronics, if they are to be placed directly below the acoustical subelements, can use the area of the entire column. This is much more area than would be permitted for a two-dimensional reconfigurability scheme in which both dimensions must be kept small. This reconfigurability scheme can be extended to allow for multiple rows for 1.25D, 1.5D, and 1.75D arrays.

High-voltage switches are readily implemented in available complementary metal oxide semiconductor (CMOS) technology. This technology is especially attractive because it allows for high-density digital control circuitry to be integrated adjacent to the controlled switch. As discussed earlier, this feature allows for very fast low-noise transitions from one configuration to the next. Other technologies such as micromachined electro-mechanical system (MEMS) switches may also be used, and this technology is not limited to CMOS.

High-voltage CMOS switches are composed of metal oxide semiconductor field effect transistors (MOSFETs). Such devices have drain, source and gate connections, where a voltage on the gate controls passage of current across the channel between the drain and source. A wider channel will have a lower switch-on resistance, which is advantageous for ultrasound imaging because it means less thermal noise is added to the receive signal. In order to create a wider channel however, it is necessary to grow the size of the device.

In a two-dimensional array, very wide devices are broken into sections called "fingers" in order to create rectangular devices that fit well underneath two-dimensional array elements. In a linear array however, longer fingers would be used. In general it is possible to judiciously layout the switching elements such that very tall and thin devices will fit underneath the array elements. In addition, due to the limited integration of transducer elements in the vertical direction (short axis) of the array, routing of signals from the center of the array to switching electronics on the top and bottom of the array could be done. This would allow for the use of more complicated control structures or for further reduction of switch-on resistance.

Apodization involves applying a set of weighting factors to the signals transmitted or received by the elements of an array. For example, the amplitude distribution along the array can be smoothed using a function such as a raised cosine to minimize the element-to-element transitions. Dynamic apodization is required to deal with the reconfigurable apertures. This can be achieved in part by using system channel apodization on the signals received from the interconnected (i.e., combined) subelements. In addition, apodization can be applied on the subelement level to give finer control.

Figure 9:
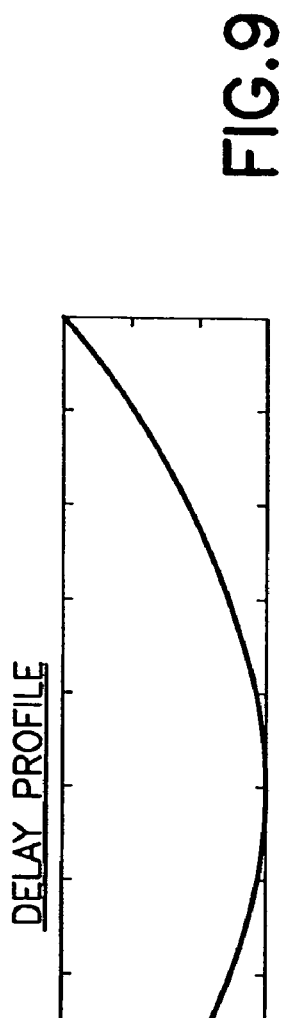
FIG. 9 is graph showing a typical delay profile for focusing at a point for a beam that is perpendicular to the transducer array and centered in the active portion of the array.
Figure 10:
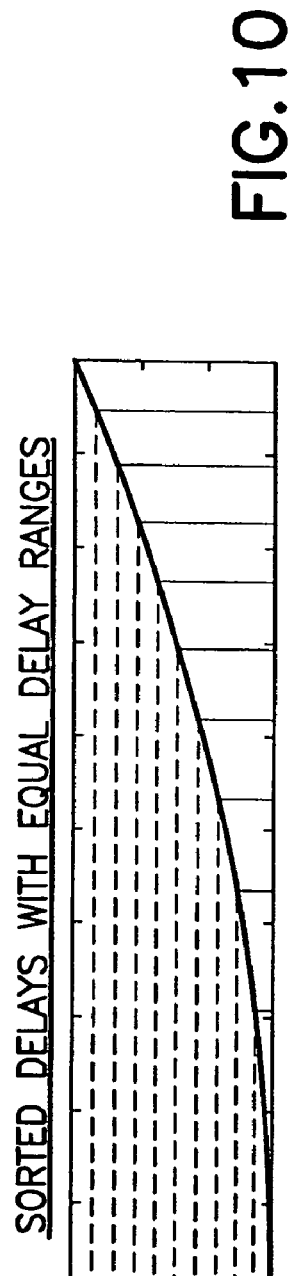
FIG. 10 is a graph showing an example of dividing into ten channels the aperture of the transducer array having the delay profile shown in FIG. 9.
Figure 11:
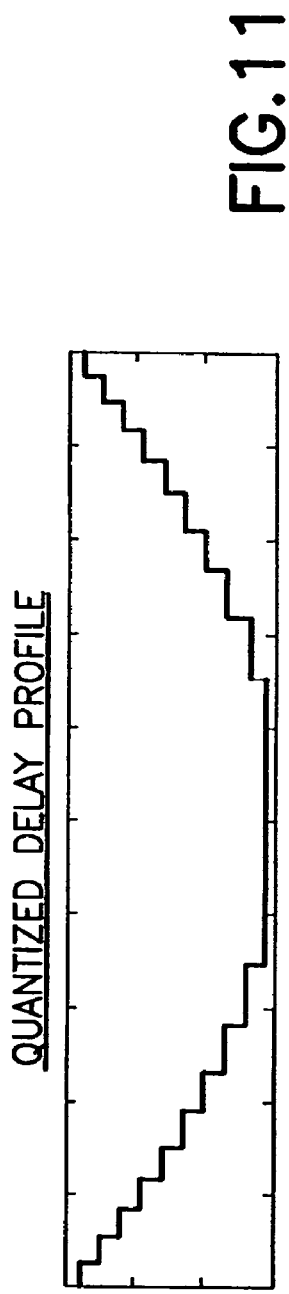
FIG. 11 is a graph showing the resulting quantized delay pattern based on equal ranges for the example of FIG. 10.

Given an array that allows the element size and location to be dynamically configured, one must determine what configuration to use. One algorithm that might be employed is to try and minimize the delay error in some sense. For a particular focal point, the delays for each of the columns could be calculated. Given these ideal delays, one can divide the aperture into N channels all having the same range of delay. This means that the maximum delay for a given channel minus the minimum delay for a given channel would be the same for every channel. Thus the columns are grouped together in a way such that columns with similar delays get assigned to the same channel. The number of columns that get assigned to a particular channel is determined by the acceptable delay range. In practice, this means that one takes the ideal delays for all the columns and sorts them. One calculates the total delay range for all the columns by subtracting the smallest delay from the largest. This total delay range is then divided by the number of channels. This gives the delay range for a given channel. FIGS. 9-11 show an example of this process.

FIG. 9 shows a typical delay profile for focusing at a point for a beam that is perpendicular to the transducer array and centered in the active portion of the array. FIG. 10 shows an example of dividing this aperture into ten channels. The time delays are sorted. The time delay range is divided into ten equal partitions. This divides the domain of the plot into ten sections. Using the sorting information, the ten domain sections can be mapped to actual columns or subelements in a reconfigurable linear array, thus determining element size and shape. FIG. 11 shows the resulting quantized delay pattern based on equal ranges.

A different version of the algorithm might divide the aperture so that the average delay errors for each channel were equal, rather than the maximum delay errors. The performance of a given array geometry might also be used in an optimizing algorithm to determine a configuration. The reconfigurable linear arrays disclosed herein are not limited to those determined by these algorithms. Rather these algorithms are intended to show examples and provide insight into how reconfigurability could work.

Figure 12:
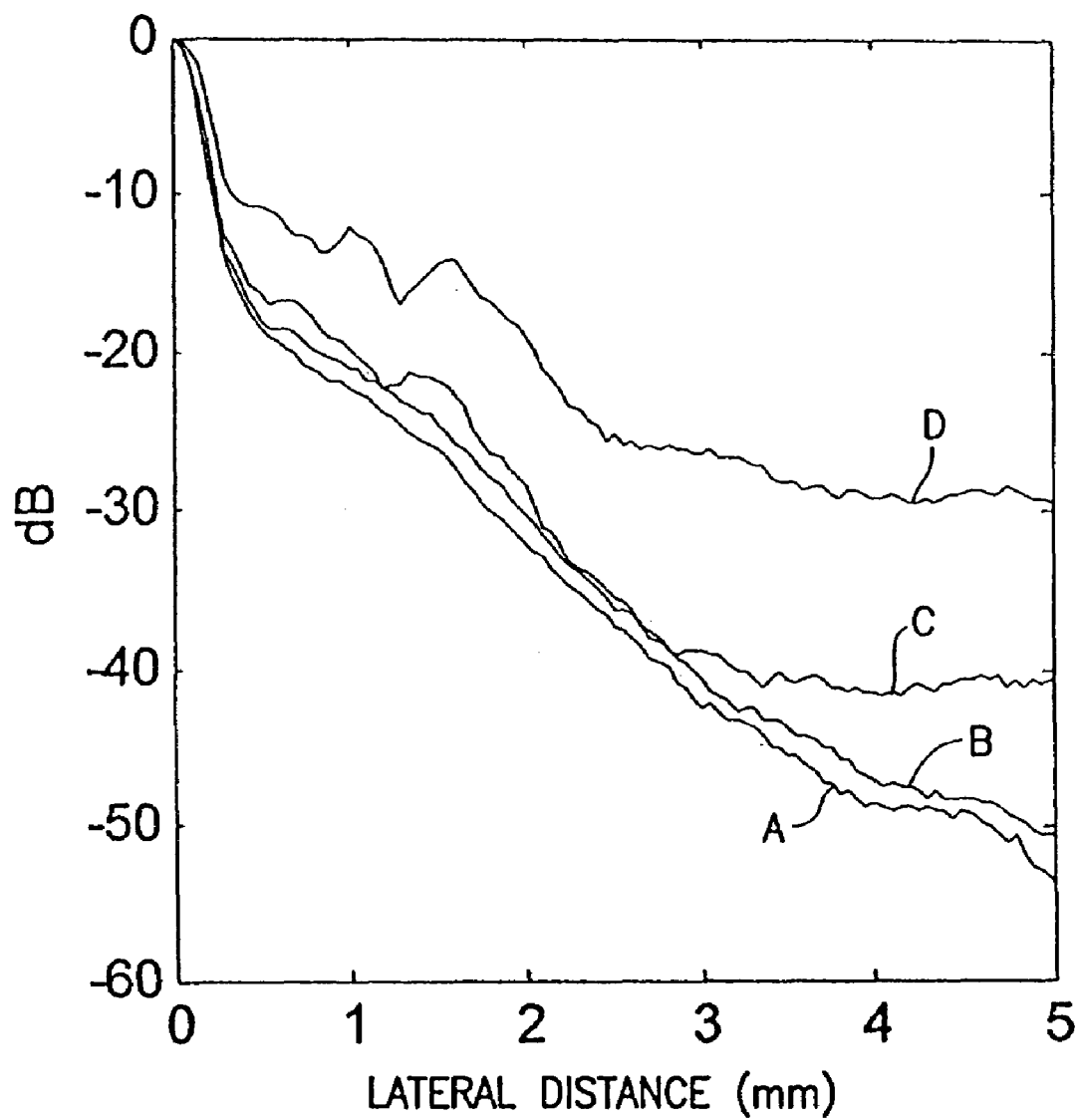
FIGS. 12-14 are graphs showing the results of simulations of radiation patterns for various reconfigurable linear arrays.
Figure 13:
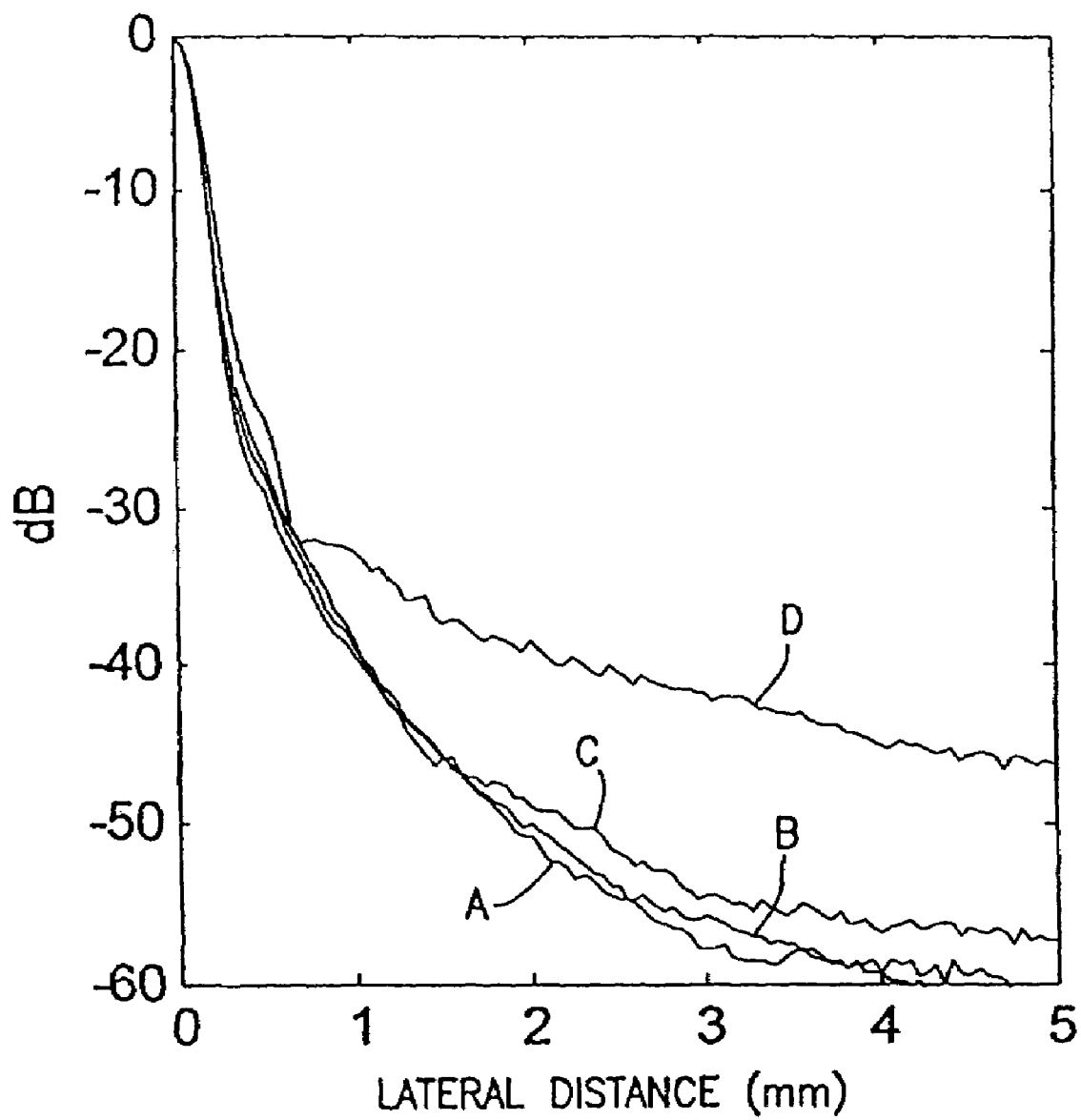
Figure 14:
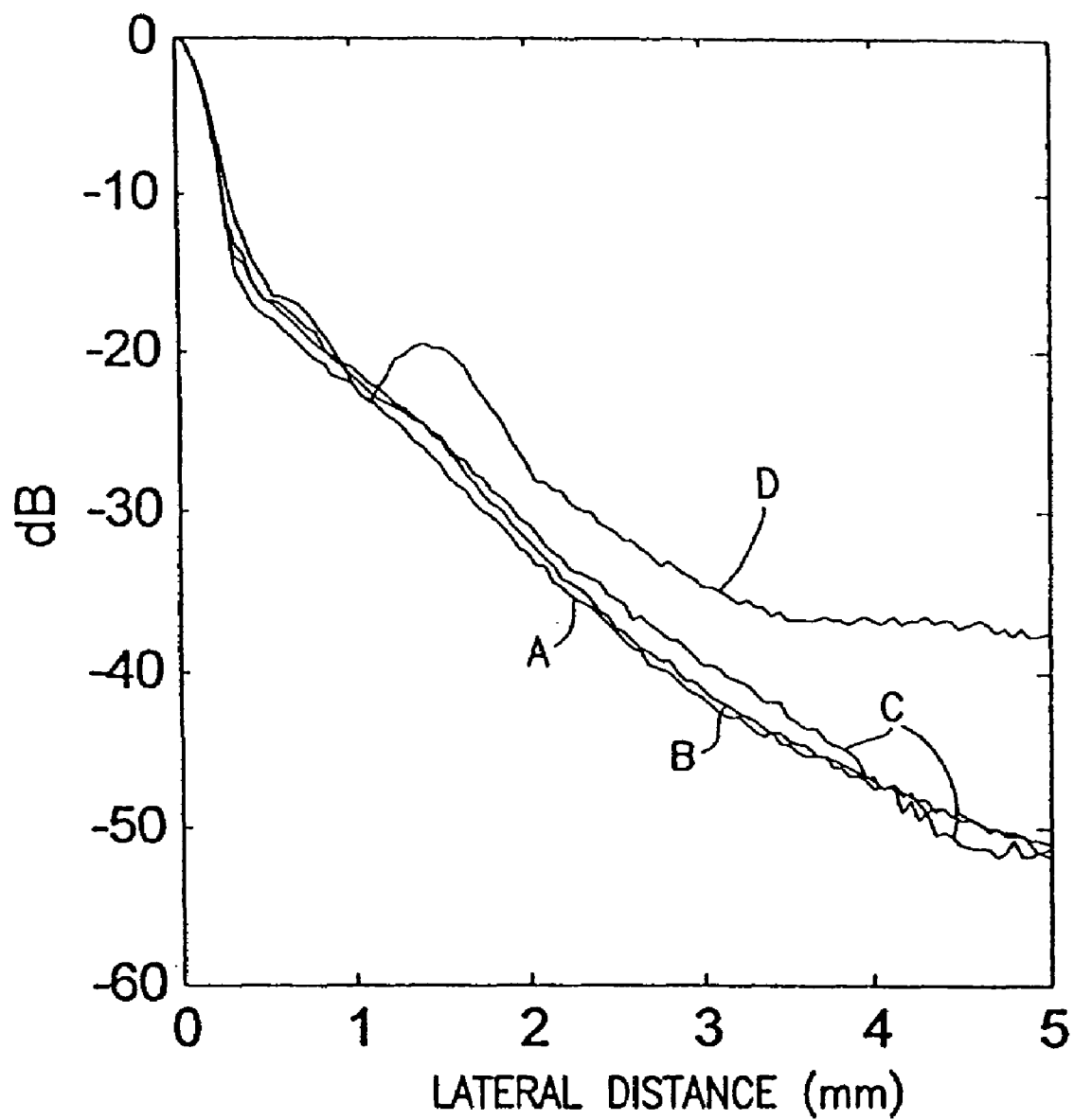

To show the possible advantages of reconfigurable linear arrays, simulations of the radiation patterns were calculated. FIGS. 12-14 show some results from these simulations. The total size of the aperture was 26 mm in the azimuthal direction and 6 mm in the elevation direction. No elevation focusing or lens was used. A 7.5 MHz, 60% fractional bandwidth pulse was used in the simulations. The transmit focal depth was 30 mm in all cases. Dynamic receive focus was used for all three cases, the depth of the receive focus being 25, 30 and 35 mm for the simulation results respectively shown in FIGS. 12, 13 and 14. The array was configured based on a point at 30 mm in all cases. Four curves are shown in each graph. Curve A represents a 128-element linear array with equal pitch (a standard imaging configuration). Curves B, C and D represent arrays based on 60, 32 and 20 channels respectively. The array was configured using the equal delay range algorithm discussed above. With as few as 32 channels, the performance was similar to that of the 128-element linear fixed-pitch array at these depths. With 20 channels, the performance is not as good and the depth of field is very small. As you move away from the transmit focus in both directions (FIGS. 12 and 14), the loss of beam quality is worse for the reconfigurable array with very few channels.

The reconfigurable linear array shown in FIG. 8 maps acoustical subelements to system channels. This mapping is designed to provide improved performance. The mapping is done through a switching network (i.e., access and matrix switches), which is ideally placed directly in the substrate upon which the cMUT cells are constructed, but can also be in a different substrate integrated adjacent to the transducer substrate. Since cMUT arrays are built directly on top of a silicon substrate, the switching electronics can be incorporated into that substrate.

Figure 15:
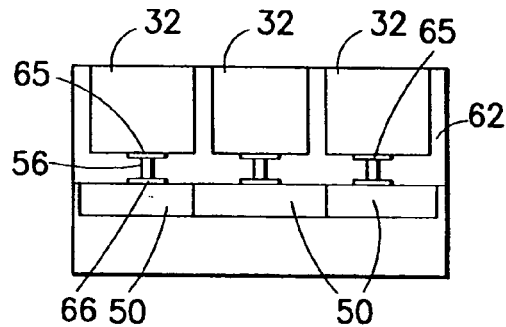
FIG. 15 is a drawing showing a cross-sectional view of a co-integrated cMUT and application-specific integrated circuit (ASIC) array.

A cross-sectional view of a co-integrated cMUT and ASIC array is shown in FIG. 15 to illustrate how the connections would be made from the ASIC to the cMUTs. As shown, a single via 56 is used to connect each cMUT acoustical subelement 32 to its counterpart CMOS electronics subelement (hereinafter "interface electronics cell") 50. The vias 56, which connect the pads 65 of the signal electrodes to respective conductive pads 66 formed on the switch ASIC, may be embedded in an acoustic backing layer 62.

As applied to the embodiment shown in FIG. 8, each interface electronics cell 50 would comprise an access switch and a matrix switch. However, for other embodiments, additional circuitry could be included in each interface electronics cell. For example, additional access and matrix switches could be included, such as an additional access switch for enabling connection to an additional access line or an additional matrix switch for connecting an acoustical subelement in one row to an adjacent acoustical subelement in another row. Also, each interface electronics cell could include a respective pulser and a respective transmit/receive switch.

Figure 16:
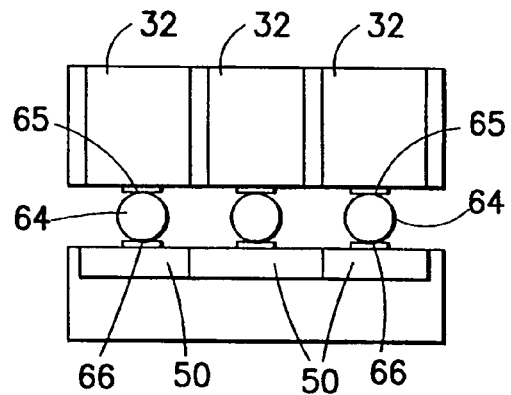
FIG. 16 is a drawing showing a cross-sectional view of a cMUT wafer connected to an ASIC switch matrix.

It is also possible to build the cMUTs on a separate substrate (e.g., a wafer) and connect them to the ASIC switch matrix separately, as shown in FIG. 16. Here for example, solder bumps 64 and conductive pads 65, 66 are used to connect the individual cMUT acoustical subelements 32 to their interface electronics counterparts 50. Other packaging techniques such as Anisotropic Conductive Film (ACF) or flexible interconnect could also be used.

Figure 17:
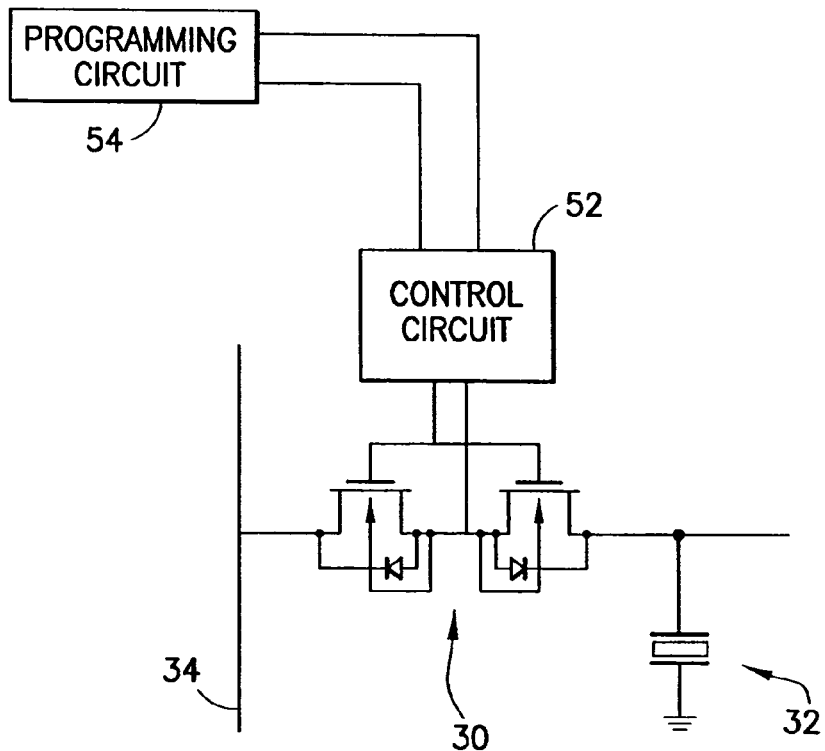
FIG. 17 is a drawing showing an access switch and circuitry for controlling the state of that access switch, as previously disclosed in U.S. patent application Ser. No. 10/248,968.

Although the access and matrix switches can be separately packaged components, it is possible to fabricate the switches within the same semiconductor substrate on which the MUT array is to be fabricated. These switches may comprise high-voltage switching circuits of the type disclosed in U.S. patent application Ser. No. 10/248,968 entitled "Integrated High-Voltage Switching Circuit for Ultrasound Transducer Array". Each switch comprises two DMOS FETs that are connected back to back (source nodes shorted together) to allow for bipolar operation. FIG. 17 shows an exemplary access switch 30; the matrix switches may comprise the same circuit. Current flows through the switch terminals whenever both FETs of switch 30 are turned on. The state of each switch is controlled by a respective switch control circuit 52, only one of which is represented in FIG. 17. The states of the switch control circuits are in turn dictated by outputs from a programming circuit 54, which programs the switch control circuits in accordance with an optimized switching configuration derived using one of the algorithms disclosed herein. A scan controller (not shown in FIG. 17) loads the optimized switching configuration into the programming circuit 54. Although use of CMOS high-voltage switches is one preferred embodiment, the invention described here is directly applicable to other switching technologies such as low-voltage switches, MEMS switches and other future switch technologies in development. The switching electronics can be built using CMOS or BiCMOS, or SOI, or MEMS or other as yet unidentified switching technology.

The various embodiments of the invention described above use reconfigurability to reduce the required number of channels for linear arrays of sensor elements made by micromachining. One way is to make the array reconfigure dynamically with depth on receive. Once the transmitted wavefront has been launched, echo data will be received for some time interval, which is usually less than 200 microseconds. During this reception time, it is advantageous to change the dimensions of the aperture to optimize the beamformation relative to the location of the traveling transmit wavefront. In this case the aperture can be grown to be larger in size to try to maintain a uniform resolution throughout the depth of the field. This requires exacting electronics, but the maximum benefit of reconfigurability is obtained. This allows similar delay errors with fewer channels than a standard fixed-pitch linear array.

Another way is to reconfigure the array for particular focal zones but without changing the array during receptions, i.e., the aperture is fixed during the receive operation. If one wishes to optimize the receive aperture for all depths, one must transmit multiple times and change either the receive aperture or the transmit and receive apertures for the individual transmits. This takes a long time and slows the imaging frame rate. In this case, the electronic implementation is easier, but the applications are limited to those where frame rate is not important or the imaging depth is very shallow. Again there is a reduction in the required number of channels with a minimal loss of beam quality at the far edges of the focal zones.

The major advantage of the invention is a reduction in the required number of channels without introducing grating lobes or significant image artifacts. Reconfigurability also allows the extreme near field to benefit from an increase in the number of channels used for beamforming.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the term "pitch" means the distance between the centerlines of two successive elements in a row of subelements.

The invention claimed is:

1. An apparatus comprising:
   a multiplicity of sensor subelements disposed in side-by-side relationship along a line to form a row;
   a multiplicity of electrically conductive access lines;
   a first multiplicity of access switches, each of said access switches electrically connecting a respective one of said sensor subelements to one of said access lines when said access switch is turned on;
   a multiplicity of matrix switches, each of said matrix switches electrically connecting a respective one of said sensor subelements to a respective adjacent one of said sensor subelements when said matrix switch is turned on;
   a multiplicity of switch state control circuits, each of said switch state control circuits controlling the states of a respective one of said access switches and a respective one of said matrix switches; and
   a programming circuit electrically connected for programming said switch state control circuits in accordance with selected switch configurations corresponding to respective apertures.

2. The apparatus as recited in claim 1, wherein each of said sensor subelements comprises a respective multiplicity of micromachined electro-mechanical devices occupying an approximately rectangular area, and each of said micromachined electro-mechanical devices comprises a respective first electrode, the first electrodes of the micromachined electro-mechanical devices making up any particular sensor subelement being electrically connected to each other and not switchably disconnectable from each other.

3. The apparatus as recited in claim 2, wherein each of said micromachined electro-mechanical devices further comprises a respective membrane overlying a respective cavity, said respective first electrode being supported by said respective membrane.

4. The apparatus as recited in claim 2, wherein each of said micromachined electro-mechanical devices comprises a respective MUT cell.

5. The apparatus as recited in claim 1, wherein each of said switch state control circuits comprises local buffering circuits for storing switch state control data corresponding to multiple switch configurations received from said programming circuit.

6. The apparatus as recited in claim 2, wherein each of said micromachined electro-mechanical devices comprises a respective second electrode underlying a respective one of said first electrodes, the second electrodes of the micromachined electro-mechanical devices making up any particular sensor subelement being electrically connected to each other and not switchably disconnectable from each other.

7. The apparatus as recited in claim 1, wherein said programming circuit programs said switch state control circuits in accordance with first and second switch configurations, said first switch configuration being effected during a first time interval and corresponding to a first receive aperture, and said second switch configuration being effected during a second time interval subsequent to said first time interval and corresponding to a second receive aperture different than said first receive aperture.

8. The apparatus as recited in claim 7, wherein said first and second switch configurations are effected dynamically during a reception time that occurs during an interval between successive transmits.

9. The apparatus as recited in claim 7, wherein said first switch configuration is effected during a transmission time and said second switch configuration is effected during a reception time.

10. The apparatus as recited in claim 7, wherein the states of said access and matrix switches are set in accordance with said first switch configuration such that those sensor subelements that are coupled to access lines form a first set of sensor elements making up said first receive aperture, and in accordance with said second switch configuration such that those sensor subelements that are coupled to access lines form a second set of sensor elements making up said second receive aperture.

11. The apparatus as recited in claim 10, wherein the pitch of the sensor elements of said first set varies across said row.

12. The apparatus as recited in claim 10, wherein the width of the sensor elements of said first set varies across said row.

13. The apparatus as recited in claim 7, wherein said first receive aperture is divided into a multiplicity of channels based on equal delay ranges or on equal means delay errors for a particular depth.

14. The apparatus as recited in claim 7, wherein said first receive aperture is divided into a multiplicity of channels based on average delay values for a range of depths of interest.

15. The apparatus as recited in claim 7, wherein said first receive aperture is divided into a multiplicity of channels based on an iterative algorithm that seeks to minimize a cost function.

16. The apparatus as recited in claim 15, wherein a metric of said cost function is beamwidth.

17. The apparatus as recited in claim 15, wherein a metric of said cost function is sidelobe level.

18. The apparatus as recited in claim 1, further comprising a second multiplicity of access switches, each of said access switches of said second multiplicity electrically connecting a respective one of said sensor subelements to one of said access lines when said access switch is turned on.

19. A device comprising:
a multiplicity of sensor subelements disposed in side-by-side relationship along a line to form a row in a first stratum;
a multiplicity of interface electronics cells disposed in side-by-side relationship along a line to form a row in a second stratum fixed relative to and underlying said first stratum, with each interface electronics cell underlying a respective sensor subelement;
a multiplicity of electrical connections, each of said electrical connections electrically connecting a respective one of said interface electronics cells to a respective one of said sensor subelements; and
a multiplicity of electrically conductive access lines,
wherein each of said unit electronics cells comprises:
an access switch that electrically connects said respective sensor subelement to one of said access lines when said access switch is turned on;
a matrix switch that electrically connects said respective sensor subelements to a respective adjacent one of said sensor subelements when said matrix switch is turned on; and
switch state control circuitry that controls the states of said access and matrix switches.

20. The device as recited in claim 19, wherein said switch state control circuitry comprises latches for storing switch state control data.

21. The device as recited in claim 19, wherein each of said sensor subelements comprises a respective multiplicity of interconnected MUT cells that are not switchably disconnectable from each other.

22. The device as recited in claim 19, wherein said multiplicity of sensor subelements and said multiplicity of interface electronics cells are co-integrated on the same substrate.

23. The device as recited in claim 19, wherein said multiplicity of sensor subelements are micromachined in or on a first substrate, and said multiplicity of interface electronics cells are integrated on a second substrate, said first and second substrates being arranged to form a stack.

24. The device as recited in claim 19, wherein said access and matrix switches are CMOS switches.

25. A system comprising:
a linear array of ultrasonic transducer subelements;
a multiplicity of matrix switches disposed to selectively electrically couple ultrasonic transducer subelements to each other to form ultrasonic transducer elements when said matrix switches are selectively turned on;
a multiplicity of electrically conductive access lines running substantially parallel to said linear array;
a multiplicity of access switches disposed to selectively electrically couple ultrasonic transducer elements to access lines when said access switches are selectively turned on;
a multiplicity of system channels; and
a switching matrix having a state whereby each of said access lines is electrically coupled to a respective one of said system channels via a multiplexer,
wherein each of said ultrasonic transducer subelements comprises a respective multiplicity of electrically connected and not switchably disconnectable MUT cells.

26. The system as recited in claim 25, further comprising a multiplicity of switch state control circuits, each of said switch state control circuits controlling the states of a respective one of said access switches and a respective one of said matrix switches; and
a programming circuit electrically connected for programming said switch state control circuits in accordance with selected switch configurations.

27. The system as recited in claim 26, wherein said programming circuit programs said switch state control circuits so that during a first time interval, sensor subelements are coupled to access lines to form a first set of sensor elements making up a first receive aperture, and during a second time interval subsequent to said first time interval, sensor subelements are coupled to access lines to form a second set of sensor elements making up a second receive aperture different than said first receive aperture.

28. The system as recited in claim 27, wherein the pitch of the sensor elements of said first set varies across said linear array.

29. The system as recited in claim 27, wherein the width of the sensor elements of said first set varies across said linear array.

30. The system as recited in claim 25, wherein each of said ultrasonic transducer subelements can be connected to each of said access lines by a respective access switch, and said switching matrix comprises a half or full cross-point switching matrix.

31. A system comprising:
a linear array of ultrasonic transducer subelements;
a multiplicity of access lines; and
a switching network comprising a first set of switches for electrically connecting selected ultrasonic transducer subelements to each other to form ultrasonic transducer elements, and a second set of switches for electrically coupling said ultrasonic transducer elements to selected access lines, said first and second sets of switches being set in accordance with a switching configuration to form an aperture, wherein said first set of switches and said second set of switches are controllable to vary the pitch and width of said ultrasonic transducer elements.

32. The system as recited in claim 31, wherein each of said ultrasonic transducer subelements comprises a respective multiplicity of micromachined ultrasonic transducer cells that are electrically connected to each other and are not switchably electrically disconnectable from each other.

33. The system as recited in claim 31, further comprising:
a multiplicity of beamformer channels; and
a switching matrix for electrically coupling selected access lines to selected beamformer channels.

34. The system as recited in claim 31, wherein pairs of said ultrasonic transducer elements that are equidistant from a beam center are electrically connected to the same access line.

35. The system as recited in claim 31, wherein each of said ultrasonic transducer subelements can be connected to each of said access lines by a respective switch, and said switching matrix comprises a half or full cross-point switching matrix.

* * * * *

UNITED STATES PATENT AND TRADEMARK OFFICE
CERTIFICATE OF CORRECTION

PATENT NO. : 7,443,765 B2
APPLICATION NO. : 11/018238
DATED : October 28, 2008
INVENTOR(S) : Thomenius et al.

It is certified that error appears in the above-identified patent and that said Letters Patent is hereby corrected as shown below:

In Column 16, Line 6, in Claim 19, delete "unit" and insert -- interface --, therefor.

In Column 17, Line 1, in Claim 27, delete "sensorelements" and insert -- sensor elements --, therefor.

Signed and Sealed this

Twenty-third Day of November, 2010

David J. Kappos
*Director of the United States Patent and Trademark Office*